United States Patent [19]
Dickerson

[11] 4,227,667
[45] Oct. 14, 1980

[54] I.V. POLE BRACKET

[76] Inventor: Henry R. Dickerson, 741 S. Chase La., Lombard, Ill. 60148

[21] Appl. No.: 948,823

[22] Filed: Oct. 5, 1978

[51] Int. Cl.³ ............................................. A47B 96/06
[52] U.S. Cl. ................................... 248/229; 24/81 B; 248/316 D
[58] Field of Search .................. 248/229, 300, 316 D, 248/226.5; 24/255 R, 81 B, 81 DM; 5/317 R; 403/346

[56] References Cited

U.S. PATENT DOCUMENTS

| | | | |
|---|---|---|---|
| 616,525 | 12/1898 | Coon | 24/81 DM |
| 725,586 | 4/1903 | Pool | 24/81 B |
| 853,544 | 5/1907 | Fernald | 24/81 B |
| 992,995 | 5/1911 | Staples | 24/255 R X |
| 1,269,734 | 6/1918 | Noland | 248/229 X |
| 1,287,554 | 12/1918 | Wood | 248/229 X |
| 1,745,548 | 2/1930 | Lerner | 248/226.5 X |
| 2,191,782 | 2/1940 | Valane | 248/229 |
| 2,523,785 | 9/1950 | Sereno | 248/229 UX |
| 3,899,149 | 8/1975 | Schneider | 248/229 X |

Primary Examiner—J. Franklin Foss
Attorney, Agent, or Firm—Blanchard, Flynn, Thiel, Boutell & Tanis

[57] ABSTRACT

Device for mounting onto a branched base conventional means for dispensing an intravenous solution. There is provided a simple and inexpensive clip for fixing to a branched, as T-shaped or L-shaped, base a rod such as that supporting the reservoir from which an intravenous solution is dispensed. A simple clip is provided with a plurality of, as three, resilient gripping means for grasping the components of said branched base whereby said clip is held against movement in all three basic directions and said clip is further provided with suitable receptacle means for receiving such rod.

10 Claims, 9 Drawing Figures

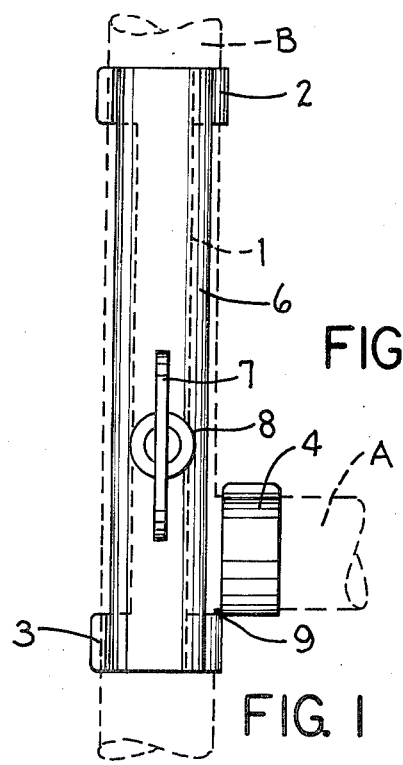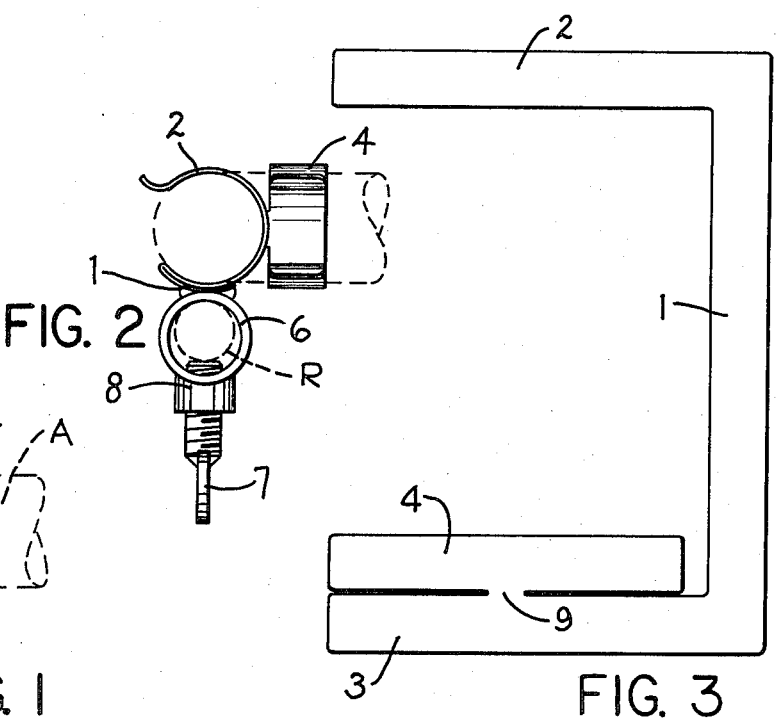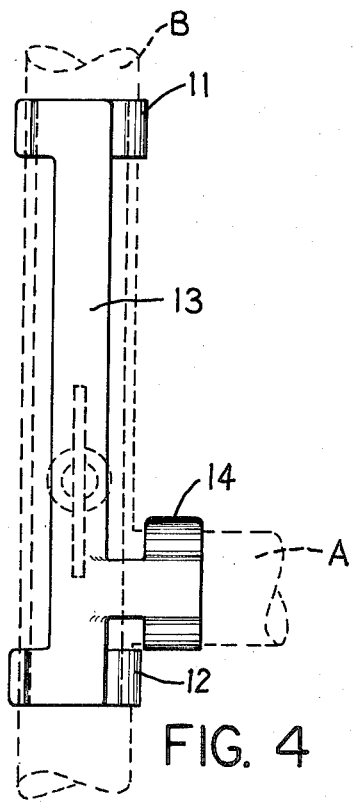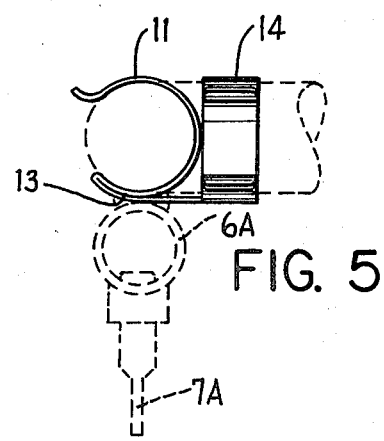

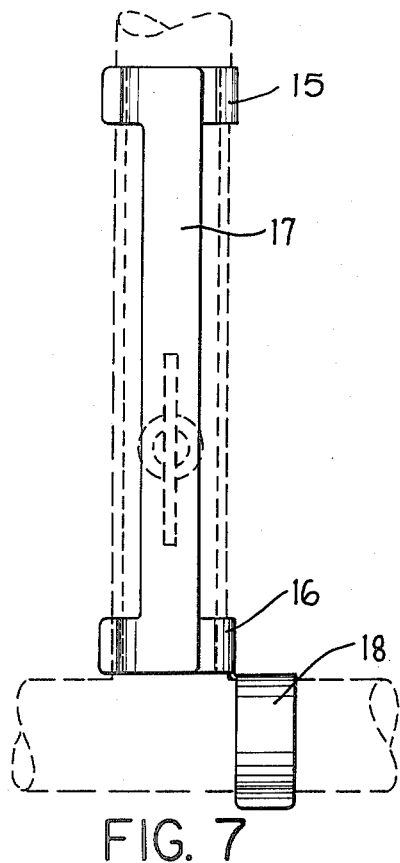
FIG. 7
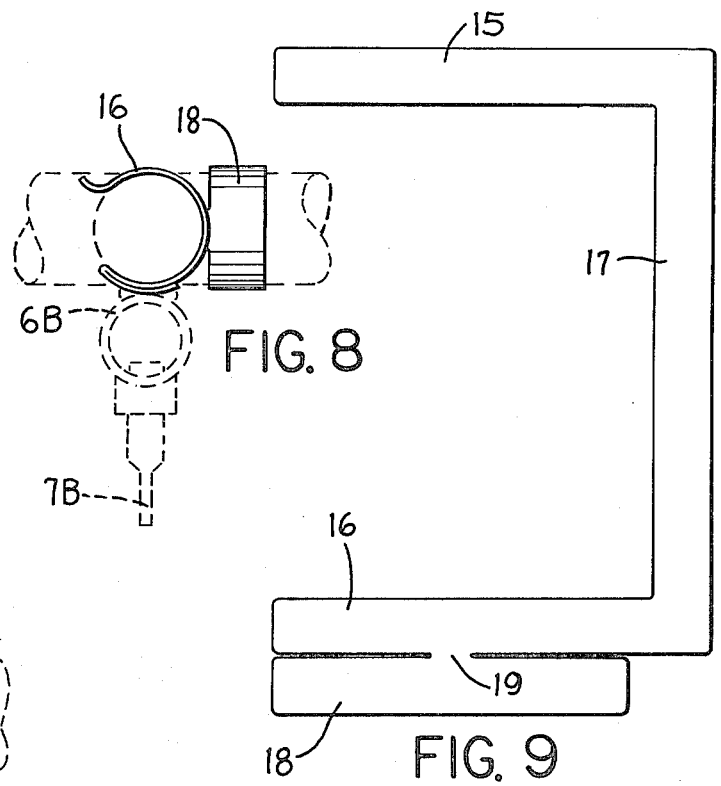
FIG. 8
FIG. 9
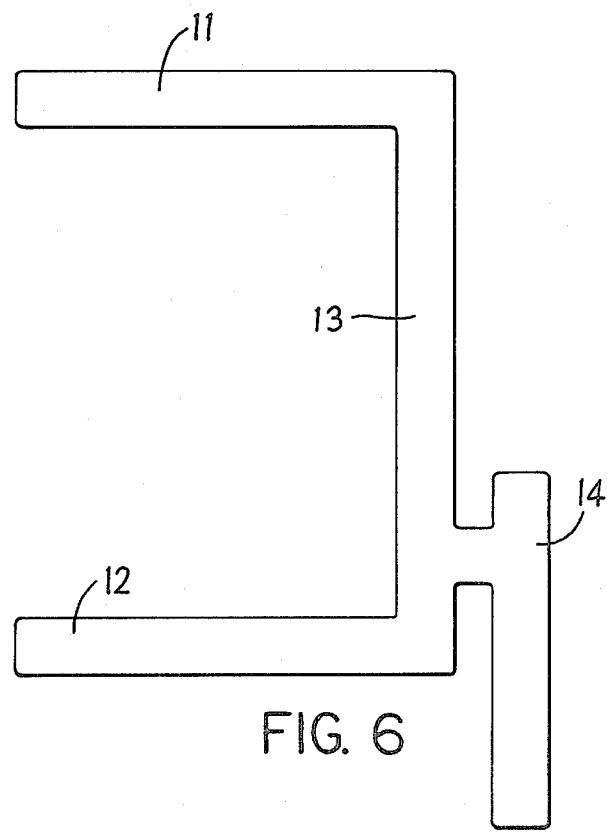
FIG. 6

I.V. POLE BRACKET

FIELD OF THE INVENTION

A clip affixable to a branched, as T-shaped or L-shaped, base and carrying a receptacle suitable for firmly receiving means such as a rod upon which is supported a reservoir for dispensing an intravenous solution to a patient.

BACKGROUND OF THE INVENTION

In the dispensing of intravenous solutions, it is conventional to support the reservoir from which such solution is dispensed on a vertically positioned rod and to support said rod through a suitable, often wheeled, base on a floor adjacent the means, as a bed or wheelchair, occupied by the patient. Where the means supporting the patient is relatively fixed, as a hospital bed, this works satisfactorily and has been standard procedure for many years. However, where the patient occupies a mobile device, such as a wheelchair, or a transport carrier such as the carrier used to transport to and from an operating room, the stand, often termed an I.V. stand, must be wheeled along with the mobile device, and this can become extremely inconvenient. Accordingly, the objects of the invention include:

1. To provide means for mounting at least the reservoir portion of an I.V. dispenser directly onto said mobile devices.
2. To provide means, as aforesaid, which will be effective without modification of the reservoir or of the rod supporting means to select the height above the patient occupied by the reservoir.
3. To provide means, as aforesaid, by which the I.V. reservoir and its supporting rod may be moved quickly and easily from the conventional base of the I.V. stand to a position on the mobile device without disconnecting the I.V. equipment from the patient, without requiring special tools and without requiring other than a very small increment of time.
4. To provide means, as aforesaid, which comprises a small, inexpensive and easily manufactured clip capable of quick attachment to the mobile device and which will receive the reservoir supporting rod of the I.V. equipment quickly, easily and rigidly.
5. To provide a clip, as aforesaid, which can be attached readily to a wide variety of mobile devices and which when so affixed will be rigid with respect thereto at least within the range of forces required for appropriate support of the I.V. equipment thereon.
6. To provide a clip, as aforesaid, which, while primarily designed and intended for application to mobile devices as above set forth, may be as desired applied to a wide variety of other patient support devices such as beds or chairs with the same characteristics and advantages as above set forth for mobile devices, providing only said further devices have T-shaped, L-shaped or similar intersections of tubular, or other elongated, material generally similar to those above referred to in connection with mobile devices.
7. To provide a clip, as aforesaid, which will be sufficiently inexpensive to manufacture that same can be applied to and left in place on all or most of the devices above mentioned without excessive expense.
8. To provide a clip, as aforesaid, which can be applied to said devices without modification of or damage to such devices and which if desired can be easily and quickly removed from such devices without leaving noticeable, if any, marks thereon.

Other objects and purposes of the invention will be apparent to persons acquainted with devices of this general type upon reading the following specification and inspection of the accompanying drawings.

BRIEF DESCRIPTION OF THE DRAWINGS

In the drawings:

FIG. 1 represents a side elevational view of one preferred embodiment of the invention with the parts of the device, as a wheelchair or transport carrier to which same is applied, indicated therein by broken lines.

FIG. 2 is a top view of the clip of FIG. 1.

FIG. 3 is a plan view of the blank from which the clip of FIGS. 1 and 2 may be stamped.

FIG. 4 is a side elevational view of another embodiment of the invention.

FIG. 5 is a top view of the embodiment shown in FIG. 4.

FIG. 6 is a plan view of the blank from which the clip of FIGS. 4 and 5 may be stamped.

FIG. 7 is a side elevational view of a further embodiment of the invention with the parts to which said clip is applied indicated in phantom.

FIG. 8 is a top view of the embodiment of the clip shown in FIG. 7.

FIG. 9 is a plan view of the blank from which the embodiments of FIGS. 7 and 8 may be stamped.

DETAILED DESCRIPTION

The invention contemplates a resilient clip which may be snapped into place onto a suitable branched, as T-shaped or L-shaped, support base which when so positioned will be rigid in all three primary directions and which is provided with a suitable receptacle for receiving and fixing with respect thereto the vertical rod upon which conventionally the reservoir is supported for dispensing an intravenous solution.

The branched support means may comprise the perpendicular relationship often found in a wheelchair where the tubing supporting the arm thereof projects horizontally from a vertically positioned tubing comprising the back thereof. Likewise a suitable branched base may be found in many transport carriers such as are used for conveying a patient into an operating room in the portion thereof where vertical support tubing extends upwardly to pallet supporting means from a horizontal tubing comprising the cart means immediately therebelow. Other components will be found in a variety of such equipment and will assume any of many specific forms such as T-, lazy-T, inverted T, L, inverted L or other similar relationships. Further, while the embodiments herein utilized assume that the branches to which it is fixed are perpendicular with respect to each other, it will be evident that same is by way of illustration only and that by suitable modification of the clip same may be made to fit branches which are at other angles with respect to each other. Likewise, while the particular problem out of which this invention arose has existed in the association of I.V. equipment with the mobile devices above mentioned, same can if desired be used in place of the more conventional floor stand on any nonmobile equipment such as a hospital bed in which there exists the same or similar branched component above described in connection with mobile devices.

Turning now to FIG. 1, there is shown a form of clip applicable to a lazy-T base, such as may be found at the juncture of the arm A and back B of a wheelchair. In this form of the clip there is provided a body portion 1 which may be grooved if desired for added stiffness and having fixed thereto resilient gripping members further described hereinafter. Said resilient gripping members may be integral therewith if the entire clip is formed from a single stamping or may be separate if preferred. Said gripping members define a curve of something over 180° of circumference and will be reversely bent at their ends to facilitate pushing onto a rod or tubing. One of such gripping members, the first gripping member 2, is fixed to the top of the body member 1 and a second gripping member 3 is fixed to the bottom thereof. Both of the gripping members are positioned to be coaxial with each other.

A third generally similar gripping member 4 is fixed to the upper edge 9 of the second gripping member 3 and positioned thereon with its central axis intersecting and perpendicular to the common axis defined by gripping members 1 and 2.

A suitable receptacle 6 is fixed to the body member 1. Same may be, as shown, tubular and open at both ends with a thumb screw 7 associated therewith for tightening onto a rod received into said receptacle or same may be provided with a bottom by which a rod may merely be positioned therein without requiring further manipulation. Such thumb screw 7 will normally be used regardless of whether or not the receptacle 6 is provided with a bottom. Said thumb screw is threaded through the side of said receptacle into position as shown. If desired, the threading through the side of the receptacle 6 may be supplemented by the use of a boss 8 fixed to the side of said receptacle which boss is threaded as a continuation of the threading through the side of said receptacle.

The clip is here positioned on horizontal and vertical frame members, preferably frame members having a circular cross section, such as the horizontal and vertical members A and B often comprising the arm and back portions of a wheelchair. The vertical rod R supporting an intravenous reservoir may be received into receptacle 6, standing on said bottom therein if one is used, and preferably held firmly in place by tightening of said thumb screw 7.

FIG. 3 shows the blank from which the clip of FIGS. 1 and 2 may be made. The manner of appropriate bending from said blank to form said clip will be self-evident to those acquainted with metal stamping techniques upon inspection of said drawings and hence no further description is needed. Said figure particularly shows the point 9 on the upper edge of the lower gripping member at which the third gripping member is attached. The numerals applied to FIG. 3 correspond to the numerals utilized for FIGS. 1 and 2 and indicate the parts of the blank shown in FIG. 3 from which the components of FIGS. 1 and 2 are formed.

Turning now to FIGS. 4–6, there is shown a generally similar clip having a body part 13 and gripping members 11 and 12 corresponding generally to the gripping members 2 and 3 of FIGS. 1 and 2 and, like said gripping members 2 and 3, are substantially spaced from each other on the body member 13, generally corresponding to the body member 1, and are coaxial with respect to each other.

The third gripping member of this embodiment, however, a gripping member 14, is here fixed at a point intermediate the gripping members 11 and 12 instead of, as in FIGS. 1 and 2, on one edge of one of said gripping members. Same is in this embodiment mounted on and projects from a portion of the body part 13, such as a portion thereof adjacent the gripping member 12. This design is intended for affixing to a lazy-T junction of the same kind as the embodiment of FIG. 1 and as further illustrated by the broken lines in FIG. 4.

A receptacle 6A which may be identical with the receptacle 6 is fixed to the body part 13 in the same manner as receptacle 6 is fixed to the body part 1 and a thumb screw 7A is associated with receptacle 6A in the same manner as the thumb screw 7 is associated with receptacle 6. Again, the supporting rod for the reservoir of a conventional I.V. device may be positioned within the receptacle 6A and firmly fixed therein by appropriate tightening of the thumb screw 7A.

As in the case of the embodiment of FIGS. 1–3, FIG. 6 here shows a blank from which the form of FIGS. 4 and 5 may be formed, the manner of such forming being fully apparent to this acquainted with the metal forming techniques involved here and hence further explanation thereof is unnecessary. The numerals in FIG. 6 indicate the parts of said blank from which the components of the clip shown in FIGS. 4 and 5 are formed.

Turning now to FIGS. 7–9, the coaxial gripping members 15 and 16 are mounted on body part 17 and correspond functionally to the gripping members 2 and 3 of the FIGS. 1–3 form. The perpendicularly positioned gripping member 18 corresponds functionally to the gripping member 4 of the FIGS. 1–3 form. This design is intended for fixing to an inverted T junction where the continuing member is horizontal and the stem of the T is vertical, such as a portion of the frame of a patient transport of the type, for example, used in hospitals. Further to illustrate the manner of such fixing, the frame in this arrangement is illustrated in broken lines in FIG. 7.

The third gripping member 18 is fixed to the lower edge of the second gripping member 16 at a point 19 in a manner generally similar to the fixing of the third gripping member 4 to the upper edge of the second gripping member 3 in the embodiment of FIGS. 1–3. The numerals in FIG. 9 indicate the parts of said blank from which the components of the clip shown in FIGS. 7 and 8 are formed.

A receptacle 6B which may be identical with the receptacle 6 is fixed to the body part 13 in the same manner as receptacle 6 is fixed to the body part 1 and a thumb screw 7B is associated with receptacle 6B in the same manner as the thumb screw 7 is associated with receptacle 6. Again, the supporting rod for the reservoir of a conventional I.V. device may be positioned within the receptacle 6B and firmly fixed therein by appropriate tightening of the thumb screw 7B.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a device for mounting an intravenous dispensing reservoir onto the frame structure of and for movement with a patient supporting device, such as a chair or table, said intravenous device having a reservoir and a rod for supporting said reservoir, the combination comprising:

a tubular support means for receiving the rod of said intravenous equipment for support thereof; and clip means comprising a pair of gripping members having a common axis and means fixing said gripping members to said tubular support in spaced relation to each other and with said tubular support means extending substantially parallel to said common axis, said gripping members being of such size and shape as to be readily snappable onto a suitable portion of said frame structure, and a third gripping member mounted fixedly with respect to said pair of gripping members and tubular support means and oriented with its axis at an angle to, and intersecting, said common axis between said pair of gripping members, whereby to permit securement of said device simultaneously to two intersecting members of said frame structure and said reservoir supporting rod.

2. The device of claim 1 wherein said third gripping member is mounted on that edge of one of said pair of gripping members which is toward the other gripping member of said pair.

3. The device of claim 1 wherein said third gripping member is mounted on that edge of one of said pair of gripping members which is remote from the other gripping member of said pair.

4. In a device for mounting an intravenous dispensing reservoir onto the frame structure of and for movement with a patient supporting device, such as a chair or table, said intravenous device having a reservoir and a rod for supporting said reservoir, the combination comprising:

a tubular support means for receiving the rod of said intravenous equipment for support thereof; and clip means comprising a pair of gripping members having a common axis and each fixed with respect to and spaced from each other along said tubular support, said gripping members being of such size and shape as to be readily snappable onto a suitable portion of said frame structure, and a third gripping member mounted fixedly with respect to said pair of gripping members and tubular support means and oriented with its axis at an angle to, and intersecting, said common axis between said pair of gripping members, said clip means further including a body member, said spaced pair of gripping members being fixed to said body member, said third gripping members being fixed to one of said body member and a said gripping member of said pair, said tubular support means being fixed to and carried by said body member.

5. The device of claim 4 wherein said pair of gripping members are at substantially opposite ends of said body member and said third gripping member is intermediate said pair of gripping members.

6. The device of claim 4 wherein said third gripping member is substantially at an end of said body member and one of said pair of gripping members is substantially between the other thereof and said third gripping member.

7. The device of claim 4 wherein said tubular support means is a generally tubular device fixed rigidly to and aligned substantially parallel with said body part.

8. The device of claim 4 wherein said third gripping member is mounted on and projects from said body member.

9. In a device for mounting an intravenous dispensing reservoir onto the frame structure of and for movement with a patient supporting device, such as a chair or table, said intravenous device having a reservoir and a rod for supporting said reservoir, the combination comprising:

a tubular support means for receiving the rod of said intravenous equipment for support thereof; and clip means comprising a pair of gripping members having a common axis and each fixed with respect to and spaced from each other along said tubular support, said gripping members being of such size and shape as to be readily snappable onto a suitable portion of said frame structure, and a third gripping member mounted fixedly with respect to said pair of gripping members and tubular support means and oriented with its axis at an angle to, and intersecting, said common axis between said pair of gripping members, including also manually tightenable means for holding said rod rigidly within said tubular support means.

10. The device of claim 9 wherein said manually tightenable means is a thumb screw threadedly related to a wall of said tubular support means.

* * * * *